United States Patent [19]

Gubernick et al.

[11] 4,285,967
[45] Aug. 25, 1981

[54] COSMETIC PREPARATION FOR REDUCING REDNESS OF BLEMISHES

[75] Inventors: Joseph Gubernick, Port Washington; Joseph Rosenstreich, Merrick, both of N.Y.; Lois A. Clapp, Hackensack, N.J.

[73] Assignee: Estee Lauder Inc., New York, N.Y.

[21] Appl. No.: 118,053

[22] Filed: Feb. 4, 1980

Related U.S. Application Data

[63] Continuation of Ser. No. 920,931, Jun. 30, 1978, abandoned.

[51] Int. Cl.$^3$ ............... A61K 31/135; A61K 31/215
[52] U.S. Cl. ................... 424/289; 424/145; 424/148; 424/154; 424/317; 424/330
[58] Field of Search ............ 424/330, 145, 154, 289

[56] References Cited

U.S. PATENT DOCUMENTS 3,968,245  7/1976  Higuchi .................. 424/330

OTHER PUBLICATIONS

Chemical Abstracts 73:33837p (1920).
Chemical Abstracts 61:13135h (1964).
Merck Index, 9th ed., 1976, p. 1309.

*Primary Examiner*—Leonard Schenkman
*Attorney, Agent, or Firm*—Blum, Kaplan, Friedman, Silberman & Beran

[57] ABSTRACT

Cosmetic compositions including a vasoconstrictor for reducing blemish redness are provided. The cosmetic compositions comprise an effective amount of phenylephrine hydrochloride in a suitable cosmetic vehicle. The cosmetic compositions of the invention are particularly useful for reducing the redness of facial blemishes.

19 Claims, No Drawings

COSMETIC PREPARATION FOR REDUCING REDNESS OF BLEMISHES

This is a continuation of application Ser. No. 920,931, filed June 30, 1978, now abandoned.

BACKGROUND OF THE INVENTION

This invention relates generally to cosmetic compositions, and more particularly to cosmetic compositions for reducing the redness of blemishes on the skin. Historically there have been various ways of treating redness of facial blemishes, such as by masking with creams, make-ups or the like. Alternatively, longer term medicinal treatment is the most desirable means for clearing up the red condition. However, it is often desirable to reduce the redness of facial blemishes in a relatively short period of time and avoid having to mask the blemish if an individual does not wish to apply an unsightly covering which may interfere with the normal application of facial make-up. Accordingly, it would be desirable to provide a cosmetic composition which would reduce the redness of skin blemishes quickly.

SUMMARY OF THE INVENTION

Generally speaking, in accordance with the invention, cosmetic compositions which reduce the redness caused by skin blemishes are provided. The cosmetic compositions of the invention comprise an effective amount of a vasoconstrictor in a cosmetic vehicle, such as a cosmetic lotion. The cosmetic vehicles of the invention include water and alcohol mixtures. These compositions may also include a humectant or an astringent. The vasoconstrictor is phenylephrine hydrochloride which is present from about 0.1 to 1.0 weight percent, based on the total weight of the composition.

Accordingly, it is an object of the invention to provide an improved cosmetic composition for reducing the redness of blemishes.

Another object of the invention is to provide an improved cosmetic composition containing a vasoconstrictor.

A further object of the invention is to provide an improved cosmetic composition containing phenylephrine hydrochloride in a cosmetic vehicle for reducing redness of blemishes.

Still other objects and advantages of the invention will in part be obvious and will in part be apparent from the specification.

The invention accordingly comprises a composition of matter possessing the characteristics, properties, and the relation of constituents which will be exemplified in the composition hereinafter described, and the scope of the invention will be indicated in the claims.

DESCRIPTION OF THE PREFERRED EMBODIMENTS

The cosmetic compositions of the invention for reducing the redness of skin blemishes comprise a cosmetic vehicle including from about 0.1 to 1.0 weight percent of a vasoconstrictor. The vasoconstrictor is phenylephrine hydrochloride and the preferred cosmetic vehicle is a water and alcohol, or hydroalcoholic vehicle.

Cosmetic compositions prepared in accordance with the invention are desirable because the vasoconstrictor, phenylephrine hydrochloride, operates to reduce the redness of facial blemishes without the need to mask the blemish prior to application of make-up. The phenylephrine hydrochloride utilized in the cosmetic composition of the invention has the molecular formula, $C_9H_{14}ClNO_2$. The structure is as follows:

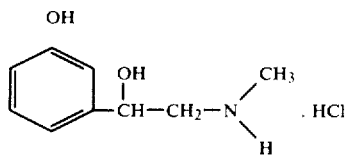

Phenylephrine hydrochloride is a white, odorless, crystalline powder having a bitter taste which is soluble in water or ethyl alcohol. It is a potent vasoconstrictor often applied locally as a decongestant in colds and conditions originating from allergies. In ophthalmic applications, it is a short acting mydriatic, useful for diagnostic and therapeutic purposes. It has also been used to prevent certain types of hypotension.

In accordance with the invention, phenylephrine hydrochloride is included in a cosmetic composition, such as a lotion in amounts ranging from about 0.1 to about 1.0 weight percent, based on the total weight of the composition. Preferably, the phenylephrine hydrochloride is present in amounts ranging from about 0.3 to about 0.7 weight percent and most preferably about 0.5 weight percent, based on the total weight of the composition.

The cosmetic vehicle may be a water and alcohol vehicle which comprises a water and alcohol mixture. The water is preferably deionized or purified water in order to avoid introducing trace amounts of reactants into the compositions. The water comprises from about 20 to about 80 weight percent of the water and alcohol mixture, and preferably, from about 30 to 50 weight percent. The alcohol fraction of the vehicle may be present from about 20 to about 80 weight percent of the water and alcohol vehicle, and preferably, from about 50 to 70 weight percent.

In the preferred cosmetic compositions of the invention, the vehicle is about 2 parts by weight of water and about 3 parts by weight of alcohol. This ratio may be varied as desired, however, too much water will not allow for suitable quick drying of the composition upon application and too much alcohol will dry too quickly.

In the preferred compositions prepared in accordance with the invention, the alcohol is ethanol. Alternatively, higher alcohols such as isopropanol may be used in place of the ethanol. A four carbon alcohol, such as butanol does not reduce the effectiveness of the compositions of the invention, however, butanol is not preferred in a cosmetic composition due to its unpleasant odor.

A humectant may also be included in the cosmetic compositions of the invention to prevent evaporation of water. Suitable humectants include propylene glycol, 1,3 butylene glycol and the like. If a humectant is included, it may be present in amounts ranging from about 1 to about 10 weight percent, based on the total weight of the composition.

Additionally, an astringent in addition to the alcohol of the vehicle may be included in the compositions of the invention. The astringent may be included from about 0.25 to about 3.0 weight percent, based on the total weight of the composition. Such suitable secondary astringents include those metallic compounds commonly used in cosmetics, such as zinc, aluminum and organic astringent compounds. Suitable metallic astringents include, for example, zinc chloride, zince acetate, aluminum potassium sulfate (Alum), zinc phenosulfonate, alcohol soluble aluminum chlorhydroxy allantoinate and copper, iron and manganese salts. The iron and manganese salts may introduce color if desired. Other organic astringent compounds which may be used include tanic acid and its derivatives, acetic, citric or lactic acids.

Additional ingredients may also be included, such as an antiseptic. Once such antiseptic found particularly useful for a facial composition is boric acid which may be included from about 1 to about 6 weight percent of the composition, based on the total weight. A fragrance may be added if desired, the primary consideration being a need for the vehicle to operate in an effective cosmetic manner. In this regard, it is desirable to add a minor amount of menthol which also imparts a cooling and stimulating sensation. The menthol may be present from about 0.005 to 2.0 weight percent, based on the total weight.

It has been found that effective results are obtained by a hydroalcoholic system including the phenylephrine hydrochloride. However, the activity producing and redness caused by blemishes is reduced more significantly when a secondary astringent compound other than the alcohol, described above, is included in the composition containing the phenylephrine hydrochloride.

The following example is illustrative of the present invention and it is to be understood that the invention is not limited thereto. All percents listed are weight percent, based on the total weight of the composition, except where otherwise noted.

EXAMPLE 1

Into a stainless steel mixing tank was added 65 parts of ethanol. The ethanol was placed under Lightnin mixer agitation and 0.1 parts menthol crystals were added and agitation was continued until the menthol crystals were dissolved. At this time 0.75 parts zinc phenolsulfonate was added under mixing conditions and agitation was continued until the mixture was clear. In a separate stainless steel container, 29.85 parts deionized water, 3.0 parts 1,3 butylene glycol, 0.5 parts boric acid, 0.5 parts phenylephrine hydrochloride and 0.3 alcohol soluble aluminum chlorhydroxy allantoinate were added under agitation which was continued until the solution was clear. At this time the water phase was added to the alcohol tank in a thin stream under continuous Lightnin mixer agitation. The product was mixed until clear and allowed to stand overnight. On the following day, the solution was filtered clear and stored in a suitable stainless steel container.

A cosmetic composition prepared in accordance with the invention was a clear, water-white liquid. The pH of the liquid at 25° C. was 4.00±0.50. The specific gravity at 25° C. was determined to be 0.933±0.01 by Troemner specific gravity chain balance.

Accordingly, a cosmetic composition effective for reducing the redness of facial blemishes may be prepared by addition of a vasoconstrictor to a cosmetic composition such as a lotion. The preferred compositions are hydroalcoholic systems including phenylephrine hydrochloride and an additional astringent, antiseptic, humectant and menthol. The cosmetic compositions are effective for reducing the redness of facial blemishes by constricting the small broken capillaries on the skin making redness less obvious. A composition prepared in accordance with the invention is effective as claimed, however, it is not claimed to be a substitute or proper treatment or an appropriate medication for clearing up skin conditions, such as acne.

It will thus be seen that the objects set forth above, among those made apparent from the preceding description, are efficiently attained and, since certain changes may be made in the above composition of matter without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A cosmetic composition for reducing the redness of skin blemishes comprising from about 20 to 40 weight percent water and from 60 to 80 weight percent ethanol; from about 0.1 to about 1.0 weight percent of a phenylephrine hydrochloride vasoconstrictor; and from about 0.25 to 3.0 weight percent of an astringent selected from the group consisting of metallic astringent compounds and organic acids, all weight percents based on the total weight of the composition.

2. The cosmetic composition of claim 1, wherein said metallic astringent compound is selected from the group consisting of zinc and aluminum compounds.

3. The cosmetic composition of claim 2, wherein said metallic astringent compound is zinc phenolsulfonate.

4. The cosmetic composition of claim 1, further including an antiseptic.

5. The cosmetic composition of claim 4, wherein said antiseptic is boric acid.

6. The cosmetic composition of claim 5, wherein said boric acid is present from about 1 to about 6 weight percent, based on the total weight of the composition.

7. The cosmetic composition of claim 1, further including a humectant.

8. The cosmetic composition of claim 7, wherein said humectant is present from about 1 to about 10 weight percent, based on the total weight of the composition.

9. A cosmetic composition for reducing the redness of skin blemishes comprising:
   a hydroalcoholic cosmetic vehicle of from about 20 to 40 parts water and from about 60 to 80 parts ethanol;
   from about 0.1 to 1.0 weight percent phenylephrine hydrochloride;
   from about 0.25 to 3.0 weight percent of an astringent selected from the group consisting of zinc and aluminum astringent compounds; and
   from about 1 to 6 weight percent of an antiseptic all weight percents based on the total weight of the composition.

10. The cosmetic composition of claim 9 further including from about 0.05 to 2.0 weight percent menthol.

11. The cosmetic composition of claim 10, further including from about 1 to 10 weight percent of a humectant.

12. A cosmetic composition for reducing the redness of skin blemishes comprising an aqueous cosmetic vehicle including an effective amount from about 0.1 to 1.0 weight percent of a phenylephrine hydrochloride vasoconstrictor and from about 0.25 to 3.0 weight percent of an astringent selected from the group consisting of metallic astringent compounds and organic acids, all weight percents based on the total weight of the composition.

13. The cosmetic composition of claim 12 wherein said metallic astringent compound is selected from the group consisting of zinc and aluminum compounds.

14. The cosmetic composition of claim 13, wherein said metallic astringent compound is zinc phenolsulfonate.

15. The cosmetic composition of claim 12, further including an antiseptic.

16. The cosmetic composition of claim 15, wherein said antiseptic is boric acid.

17. The cosmetic composition of claim 16, wherein said boric acid is present from about 1 to about 6 weight percent, based on the total weight of the composition.

18. The cosmetic composition of claim 12, further including a humectant.

19. The cosmetic composition of claim 18, wherein said humectant is present from about 1 to about 10 weight percent, based on the total weight of the composition.

* * * * *